United States Patent [19]

Michel et al.

[11] 4,081,426

[45] Mar. 28, 1978

[54] PREPARATION OF AMINOPLASTS

[75] Inventors: Walter Michel; Hans Hönel, both of Frankfurt am Main; Manfred Schön, Dudenhofen, all of Germany

[73] Assignee: Cassella Farbwerke Mainkur Aktiengesellschaft, Germany

[21] Appl. No.: 677,131

[22] Filed: Apr. 15, 1976

[30] Foreign Application Priority Data

Apr. 15, 1975 Germany ............................. 2516349

[51] Int. Cl.² ............................................ C08G 12/26
[52] U.S. Cl. .............................................. 260/67.6 R
[58] Field of Search ...................... 260/67.6 R, 67.6 C

[56] References Cited

U.S. PATENT DOCUMENTS 3,392,150  7/1968  Groll ............................... 260/67.6 R

FOREIGN PATENT DOCUMENTS 468,677  7/1937  United Kingdom.

Primary Examiner—Thomas De Benedictis, Sr.
Attorney, Agent, or Firm—Connolly and Hutz

[57] ABSTRACT

Aminoplast preparation is greatly speeded by condensing an aminotriazine such as melamine with formaldehyde and etherifying alkanol under superatmospheric pressure and at a temperature between about 80° and about 130° C.

4 Claims, No Drawings

PREPARATION OF AMINOPLASTS

Etherified methylol-aminotriazine aminoplasts have become increasingly important in the course of recent industrial development. They are being employed in ever increasing amounts in numerous fields, for example as crosslinking agents in water-soluble and solvent-soluble lacquer compositions, as cross-linking agents for latices and dispersion binders which contain hydroxyl groups, for the manufacture of moulding compositions, as constituents of waterproof adhesives for gluing veneers, in the manufacture of laminates and edge veneers, and for surfacing sheet material. Alkanol-etherifed (mainly methyl-etherified) methylol-aminotriazines are also used in the paper industry for the production of surfaces which are dry and exhibit wet strength and for improving paper coatings especially for rendering them waterproof, and in the textile industry products of this type are employed as permanent finishing agents. For use of the alkanoletherified methylol-aminotriazines in all of the abovementioned fields, it is particularly desirable that cured, aminoplast-crosslinked resins formed therefrom by a curing process effected by the action of acid and/or heat should exhibit surface hardness, scratch-resistance, stability to dry heat, steam resistance, adhesion and elasticity.

The etherified methylol-aminotriazines have been manufactured by reacting the aminotriazine with formaldehyde and the alkanol used for etherification, in the presence of a suitable amount of acid and at ambient or atmospheric pressure in containers that were not pressurized and the reaction takes a substantial time especially when etherified methylol-aminotriazines with a low degree of methylolation are to be manufactured. If an attempt is made to increase the rate of reaction by raising the concentration of acid it is necessary after the reaction has taken place and the acid has been neutralised, to remove the salt thus formed from the resulting precondensate, and this offsets the time gained by the higher rate of reaction. This disadvantage is the more inconvenient since it is, in particular, resins which have a low formaldehyde content which offer substantial advantages when they are used in the laminate sector; they display higher reactivity and give off considerably less formaldehyde during curing, both of which features substantially facilitate their use. A further disadvantage of the prior art manufacturing processes is that they do not yield precondensates with a low degree of methylolation which are stable on storage, that is to say which do not tend to crystallise on prolonged storage.

Among the objects of the present invention is the shortening of the overall time required for the preparation of aminoplasts, including high quality aminoplasts.

The foregoing as well as additional objects of the present invention will be more fully understood from the following description.

It has now been found that the foregoing pre-condensates are much more readily formed by conducting the condensation under a superatmospheric pressure of at least 0.1, preferably 0.5 atmospheres gauge and at a temperature of between 80° and 130° C., using alkanols having up to four carbon atoms.

The reaction then generally takes place so rapidly that it can be terminated within 0.2 to 20 minutes. Preferably 0.77 - 3 mols of formaldehyde and 2.5 - 7 mols of the alkanol or mixture of alkanols are used per $-NH_2$ mol in the aminotriazine. The products thus obtained have from about 0.7 to 2 methylol groups per $-NH_2$, with about 30 to about 60% of the methylol groups etherified. In order to effect a specific degree of condensation, the amount of water added to the reactants is preferably varied in a range from 0 to 3 mols per $-NH_2$ mol in the aminotriazine. To manufacture products which have a particularly low degree of condensation, it is preferable to carry out the reaction with anhydrous reactants. Benzoguanamine and especially melamine are aminotriazines which react advantageously according to the present invention.

Examples of alkanols which are suitable for use according to the present invention are primary and secondary alcohols such as methanol, ethanol, propanol, n-butanol, butan-2-ol, isobutanol, and ether-alcohols including methoxyethanol, ethoxyethanol, methoxypropanol and methoxyisopropanol.

Mixtures of alkanols can be used to etherify methylol-aminotriazines with mixed ether groups.

The use of methanol or of a mixture of alkanols containing at least 40 mol % of methanol, is particularly preferred.

The preferred temperature range for the pre-condensation reaction is from about 85° to about 115° C. When the higher of the foregoing alkanols are used the boiling point of the reaction mixture under normal pressure can be above 80° and even above 90° C. In this case a super atmospheric pressure of at least 0.1, preferably 0.5 atmospheres is developed in the apparatus by heating the reaction mixture to a sufficiently high temperature. It is not clear exactly how the reaction mechanism is modified when the reaction is conducted in the foregoing manner, but many comparisons have shown that in each case the use of the superatmospheric pressure as well as the foregoing temperature sharply reduces the reaction time.

The process of the present invention is preferably carried out at a pH between 4.5 and 6.5. This pH is best achieved by adding a strong inorganic or organic acid in amounts of about 0.1 to 1 part per thousand to the reaction batch. Acids which can be so employed are inorganic acids such as for example sulphuric acid, nitric acid, hydrobromic acid, hydrochloric acid, hydrofluoric acid hydriodic acid, as well as compounds from which these acids are liberated under the reaction conditions, or organic acids of comparable acid strength, such as, for example, sulphonic acids, formic acid or halogenoacetic acids.

While the above pH values can be developed with weaker acids, it is advantageous to work with stronger acids since smaller molar amounts of these are required and the salt obtained after neutralisation can then generally remain in the reaction product without being troublesome during use of the pre-condensates or in the cured product.

The process of the present invention can optionally be carried out in the presence of inert organic solvents. Examples of suitable inert organic solvents are: lower aromatic hydrocarbons, aliphatic ethers, substituted amides, such as dimethylformamide, and tertiary alcohols, such as tert.-butanol.

The desired pre-condensates can be manufactured in a disproportionately short reaction time by the process of the present invention. Compared with the standard manufactoring processes the process of the present invention requires only 1/50 to 1/60 of the reaction period. This great saving in time is surprising and is much more than would be expected on the basis of the reaction temperature alone. As a result of the saving in reaction time the space-time yield for the process is substantially increased and there is, in addition, a large saving in energy. It was also not to be foreseen that such striking increase in reaction rate could be effected without more of the catalytically active acid. The extremely small amounts of salt left in the pre-condensate is thus no greater than usual and in most cases these do not have to be removed since they do not interfere with storage or use of that pre-condensate. Such removal would call for a filtration and washing operation, which of course is associated with a loss in yield and a problem with the disposal of the salts thus collected.

The high reaction rates achieved with the new process make it possible to carry out the manufacturing process in a continuous manner, a technique which has not been practised according to the conventional procedures because of the relatively long reaction times. When the process of the present invention is carried out continuously, there is, in addition to the advantages mentioned, a great saving in equipment inasmuch as large amounts of the pre-condensates can be made in relatively small-sized apparatus.

The process of the present invention is also extremely flexible and can be adapted to wide variations of the degrees of methylolation, of etherification and of condensation. Thus, for example, it is possible without difficulties and in a short reaction time to manufacture etherified methylolaminotriazines with an average analytical value of only 0.7 methylol groups per —NH$_2$ mol in the aminotriazine. The prior art has generally considered it necessary to boil the reaction batch under reflux for many hours in order to achieve this product, since the rate of the prior art reaction with the small amount of formaldehyde needed is extremely low. This is possibly due to the fact that the small amount of formaldehyde first immediately reacts with the large amount of aminotriazine, forming a small amount of more highly methylolated aminotriazines and the statistical distribution of the methylol groups to all the aminotriazine molecules of the batch takes place quite slowly.

The etherified methylol-aminotriazines made pursuant to the present invention also display, in contrast to the analogous products obtained according to prior art condensation, an exceptionally small tendency to crystallise. The products obtained according to the present invention can thus be stored over prolonged periods and even at pH values of more than 8, without detracting from their usefulness.

The degree of etherification and of condensation of the pre-condensates can be regulated, inter alia, in a simple manner by means of the amount of water added to the reactants. In this case also it is a particular advantage of the present invention that it is possible to manage with reaction times of about 5–10 minutes even when pre-condensates with a relatively high degree of condensation are manufactured. The curing characteristics, the viscosity, the compatibility with the reactants and the extent to which the products can be diluted with the appropriate solvents, can be varied and adapted to industrial requirements, by the choice of alkanols which are employed for etherification of the methylol-aminotriazines. The pre-condensates made according to the present invention are therefore very suitable for all the uses mentioned above. The process of the present invention is particularly advantageous for the production of surface-coating materials, especially for coating chipboards, and in the manufacture of laminates and edge veneers, because the etherified aminoplast compounds with low and average degrees of methylolation, which are readily accessible using the present invention, display a particularly high elasticity.

The percentages given in the examples which follow are percentages by weight. The solid content indicated in the examples is determined by drying a sample of about 2 g. of solution at 120° C. for 1 hour and weighing the residue. The flow times quoted to indicate the viscosity in the examples are flow times according to 4/DIN 53211, that is to say that were determined by means of DIN flow cups according to DIN 53211. Examples 1 to 47 illustrate the manufacture, according to the invention, of valuable resins which are outstandingly suitable as crosslinking agents for binders for nonwovens, lacquer binders, wood glues for veneering wooden materials for the production of laminates, as moulding compositions and for permanent finishing in the textile and paper industry, and Examples 48 to 52 illustrate the use of the products manufactured according to the present invention.

EXAMPLE 1

316.8 g. of melamine, 312.4 g. of paraformaldehyde (90% strength 10% water), 1,126.6 g. of methanol and 1.34 g. of p-toluenesulphonic acid are introduced into a stainless steel pressure vessel provided with a stirrer, a thermometer and a pressure gauge. The vessel is then sealed and heated to 110° C. in an oil bath while stirring (this takes 43 minutes) and is stirred for a further 12 minutes at this temperature. The internal pressure at 110° C. is 3.5 atmospheres gauge. 10 g. of a 20% strength sodium carbonate solution are then rapidly pumped into the vessel and the reaction mixture cooled to room temperature. The pH value of the reaction mixture is subsequently adjusted to 8.5 with sodium bicarbonate solution and the resulting colourless mass is concentrated by evaporation until its solids content is 65.5%.

This gives 640 g. of a viscous resin mixture which is insoluble in water but can be diluted with methanol to give a clear solution.

EXAMPLE 2

The procedure of example 1 is repeated but this time the reaction mixture is heated to 100° C. in the course of 30 minutes and is stirred for 1 minute at this temperature, an internal pressure of 2.5 atmospheres gauge being thus developed, and the evaporation effected until the product has a solids content of 87%.

This gives 630 g. of a clear, viscous melamine resin which is miscible with water in all proportions and contains 3.7 mols of formaldehyde and 2.4 mols of methoxy groups per mol of melamine.

EXAMPLE 3

316.8 g. of melamine, 312.4 g. of paraformaldehyde (90% strength), 1,126.6 g. of methanol, 110.0 g. of water and 1.34 g. of p-toluenesulphonic acid are heated, in a sealed stainless steel pressure vessel, whilst stirring, to 100° C. in the course of 20 minutes and 10 g. of a saturated sodium bicarbonate solution are then added immediately. Further working up is carried out as described in Example 1 to give 610 g. of a highly viscous resin mixture which has a solids content of 80.6% and is soluble in water. It solidifies on prolonged standing in the cold to a crystal slurry, which on warming reverts to a clear solution.

Analysis: 3.48 mols of formaldehyde and 1.65 mols of OCH$_3$ per mol of melamine.

EXAMPLE 4

316.6 g. of melamine, 193 g. of paraformaldehyde (90% strength), 1,289 g. of methanol, 67 g. of water and 1.5 g. of p-toluenesulphonic acid are heated, in a sealed stainless steel pressure vessel, whilst stirring, to 100° C. in the course of 20 minutes, an internal pressure of 2.3 atmospheres gauge developing. The mixture is then stirred at 100° C. for a further 15 minutes and subsequently 13 g. of saturated sodium bicarbonate solution are added. Working up is carried out as in the preceding examples and gives 675 g. of a very viscous colourless clear resin mixture (solids content 76.6%) which can be diluted to a limited extent with water at room temperature.

EXAMPLE 5

The procedure is as in Example 3 but, after the temperature of 100° C. is reached the mixture is stirred for 5 minutes at this temperature and then treated with sodium bicarbonate solution. When the resulting solution is worked up this gives 780 g. of a clear, colourless, viscous resin mixture which has a solids content of 82.0% and is miscible with water in all proportions.

Analysis: 3.58 mols of formaldehyde and 2.6 g. mols of OCH$_3$ per mol of melamine.

EXAMPLE 6

316 g. of melamine, 586 g. of paraformaldehyde (90% strength), 220 g. of water, 1,127 g. of methanol and 2.0 g. of p-toluenesulphonic acid are heated, in the reactor described in Example 1, while stirring, to 100° C. in the course of 20 minutes, the mixture is stirred for 5 minutes at this temperature and 9 g. of saturated sodium bicarbonate solution are then added. After working up as described in Example 1, 832 g. of a colourless, highly viscous resin mixture (solids content 95.4%), which is miscible with water in all proportions, are obtained.

Analysis: 6.0 mols of formaldehyde and 2.8 mols of OCH$_3$ per mol of melamine.

EXAMPLE 7

316.8 g. of melamine, 312.4 g. of paraformaldehyde (90% strength), 1,126.6 g. of methanol, 110.0 g. of water, and 0.844 g. of concentrated nitric acid are heated, in a sealed stainless steel pressure vessel, whilst stirring, to 100° C. in the course of 20 minutes and the mixture is stirred for a further 5 minutes at this temperature. 10 g. of saturated soldium bicarbonate solution are then added. Further working up is carried out as described in Example 1. The resin obtained after working up substantially corresponds to that obtained in Example 5.

Yield: 659 g. of resin, (residue on baking = 94.3%).

EXAMPLE 8

The procedure is as described in Example 7 but the amount of nitric acid employed is reduced to half. 785 g of a resin (residue on baking = 75.3%) which can be diluted in any proportion with the water, are obtained.

EXAMPLE 9

The procedure is as described in Example 7 but the amount of nitric acid employed is reduced to ¼. The resin obtained is also miscible with water in all proportions.

Yield: 792 g of resin (residue on baking = 75.0%).

EXAMPLE 10

316 g of melamine, 312 g of paraformaldehyde (90% strength), 1,127 g of methanol, 40 g of water and 0.5 g of nitric acid ($d = 1.4$) are heated is a sealed stainless steel vessel, whilst stirring, to 90° C in the course of 20 minutes and the mixture is then stirred for 5 minutes at this temperature, the internal pressure rising to 1.6 atmospheres gauge. 7 g of a saturated sodium bicarbonate solution are then added and the mixture is then cooled. On filtering the resulting reaction mixture, 50 g of undissolved melamine are recovered. The filtrate is concentrated to give a water-soluble 74% strength viscous resin.

Yield: 644 g.

EXAMPLE 11

The procedure is as in Example 10 but the mixture is heated to 100° C and stirred for 3 minutes at this temperature. After neutralising and cooling, there is obtained a fully reacted clear solution which can be diluted in any proportion with water. Concentrating gives 800 g of a 75% strength resin solution.

EXAMPLE 12

The reactants of Example 11 were heated to 100° C, but stirred at this temperature for only 30 seconds and then neutralised and cooled. After evaporating, 800 g of a 71% strength clear resin solution are obtained. The product is miscible with water in all proportions.

EXAMPLE 13

474 g of melamine, 312 g of paraformaldehyde (90% strength), 1,600 g of methanol and 390 g of a solution of 36% of formaldehyde and 20% of methanol and 44% of water are heated, in a sealed stainless steel vessel to 95° C, whilst stirring. The internal pressure rises to 1.4 atmospheres gauge. Thereafter a mixture of 0.65 g of nitric acid ($d = 1.4$) and 26 g of methanol is added, the mixture is stirred for a further 10 minutes at 95° C, 10 g of a saturated aqueous solution of sodium bicarbonate are then added and the mixture is subsequently cooled. The pH value of the resulting clear solution is adjusted to 8.4 with saturated sodium bicarbonate solution and the adjusted solution is evaporated to a solids content of 75%. Yield: 1,225 g. of a product miscible with water in all proportions.

Analysis: 3.5 mols of formaldehyde and 2.2 mols of OCH$_3$ per mol of melamine.

EXAMPLE 14

316 g of melamine, 312 g of paraformaldehyde (90% strength), 1,236 g of methanol and 40 g of water are heated, in a sealed stainless steel vessel whilst stirring, to 100° C in the course of 20 minutes, a pressure of 2.4 atmospheres gauge being developed. A mixture of 0.5 g of nitric acid and 4 g of methanol is then added and the reaction mixture is stirred for a further 5 minutes at 100° C and finally neutralised by adding 7 g of saturated sodium bicarbonate solution. The resulting clear solution is adjusted to a solids content of 75%. Yield: 810 g of a resin mixture having a viscosity of 170 seconds in a 4 mm flow cup at 20° C.

Analysis: 3.35 mols of formaldehyde and 2.52 mols of OCH$_3$ per mol of melamine.

EXAMPLE 15

The procedure is as in Example 13, but after addition of the acid the mixture is stirred for only 5 minutes at 95° C. After working up as in Example 13, 1,190 g of a 75% strength clear solution with a viscosity of 150 seconds (4 mm flow cup at 20° C) are obtained filtration being unnecessary.

EXAMPLE 16

The procedure is as in Example 15 but the mixture is heated to only 90° C and after addition of the acid is stirred for 5 minutes at 90° C. After filtration and working up as in Example 15, 1,170 g of a 75% strength clear solution are obtained. The viscosity of this solution is 185 seconds (4 mm flow cup at 20° C).

EXAMPLE 17

474 g of melamine, 248 g of paraformaldehyde (90% strength), 1,600 g of methanol and 310 g of a mixture containing 37% of formaldehyde, 20% of methanol and 43% of water are heated to 95° C in a sealed stainless steel vessel, whilst stirring. A mixture of 1.2 g of nitric acid ($d = 1.4$) and 26 g of methanol is then added and the reaction mixture is stirred for 5 minutes at 95° C an excess pressure of 1.5 atmospheres developing and the mixture is then rendered neutral with 30 g of a saturated sodium bicarbonate solution and cooled. 9 g of undissolved melamine are filtered off from the cooled solution and the latter is concentrated to a solids content of 75%.

The yield is 1,060 g. The viscosity of the final product at 20° C, is 315 seconds, measured in a 4 mm flow cup.

Analysis: 2.8 mols of formaldehyde and 1.4 mols of $OCH_3$ per mol of melamine.

EXAMPLE 18

474 g of melamine, 215 g of paraformaldehyde (90% strength), 1,600 g of methanol and 268 g of a mixture consisting of 37% of formic acid, 20% of methanol and 43% of water are heated in a sealed container to 100° C, a mixture of 1.2 g of nitric acid ($d = 1.4$) and 26 g of methanol is then added and thereafter the reaction mixture is stirred for 5 minutes at 100° C and finally rendered neutral with 30 g of saturated sodium bicarbonate solution. After cooling, 17.5 g of melamine are filtered off from the solution and the filtrate is worked up to give 1,000 g of a 75% strength solution which is miscible with water in all proportions but crystallises out after some time.

EXAMPLE 19

474 g of melamine, 248 g of paraformaldehyde (90% strength), 1,600 g of methanol and 310 g of a mixture consisting of 37% of formaldehyde, 20% of methanol and 43% of water are heated at up to 95° C, whilst stirring under an excess pressure of 1.5 atmospheres. A solution of 1.2 g of concentrated nitric acid in 26 g of methanol is then pumped in, the mixture is stirred for 9 minutes at this temperature, and subsequently the pH value is adjusted to 9.5 with 30 g of saturated sodium bicarbonate solution. After cooling and evaporation a clear solution having a solids content of 75% is obtained. Yield: 1,120 g. The viscosity of this product in a 4 mm flow cup at 20° C, is 190 seconds and it can be diluted in any proportion with water.

Analysis: 2.6 mols of formaldehyde and 1.8 mols of $OCH_3$ per mol of melamine.

EXAMPLE 20

The procedure is as in Example 19 but the mixture is stirred for 11 minutes, instead of 9 minutes, at 95° C. Analogous working up gives 1,095 g of a product which can be diluted in any proportion with water and which has a viscosity of 215 seconds (measured in a 4 mm flow cup at 20° C) and a solids content of 75.7% (residue on baking for 1 hour at 120° C).

Analysis: 2.8 mols of formaldehyde and 1.7 mols of $OCH_3$ per mol of melamine.

EXAMPLE 21

Example 20 is repeated on a scale 16.6 times as great. The resulting product adjusted to a solids content of 75% is clear and can be diluted in any proportion with water. Its viscosity in a 4 mm flow cup is about 250 seconds at 20° C.

EXAMPLE 22

118,500 g of melamine, 411,000 g of methanol, 63,000 g of paraformaldehyde (90% strength) and 93,000 g of a mixture consisting of 37% of formaldehyde, 20% of methanol and 43% of water are heated to 95° C in a sealed container whilst stirring. The mixture is acidified at this temperature with 300 g of concentrated nitric acid and stirred for 11 minutes at 95 to 99° C and under an excess pressure of 2.4 to 2.6 atmospheres and the pH value is then adjusted to 9.3 with 7,500 g of saturated sodium bicarbonate solution. The resulting product to a solids content of 75% has a viscosity of 170 seconds (4 mm flow cup at 20°). The properties of the product substantially agree with those of the product obtained according to Example 20.

EXAMPLE 23

474 g of melamine, 427 g of paraformaldehyde and 2,000 g of methanol are heated to 95° C in a sealed container whilst stirring, and 1.2 g of nitric acid ($d = 1.4$), dissolved in 26 g of methanol, are then added. The mixture is stirred for 10 minutes at 95° to 98° C under an excess pressure of 1.75 to 1.9 atmospheres gauge, and the pH value is then adjusted to 9.8 by adding 30 g of saturated sodium bicarbonate solution. The product is adjusted to a solids content of 76%, yield 1,142 g, and then has a viscosity of 440 seconds (4 mm flow cup at 20° C). It can be diluted in any proportion with water.

Analysis: 3.1 mols of formaldehyde and 2.0 mols of $OCH_3$ per mol of melamine.

EXAMPLE 24

The procedure is as in Example 23 but 1.5 g of nitric acid ($d = 1.4$) are employed. A clear resin solution (yield 1,145 g) which can be diluted in any proportion with water and which has a solids content of 75.9% and a viscosity of 193 seconds (4 mm flow cup at 20° C) is formed.

EXAMPLE 25

The procedure is as in Example 13 but the amount of methanol is increased from 1,600 g to 2,000 g. The product adjusted to a solids content of 75% (yield 1,120 g) has a flow cup viscosity of 150 seconds (4 mm flow cup at 20° C) and can be diluted in any proportion with water.

Analysis: 3.3 mols of formaldehyde and 1.4 mols of $OCH_3$ per mol of melamine.

EXAMPLE 26

474 g of melamine, 427 g of paraformaldehyde (90% strength), 2,000 g of methanol and 1.5 g of concentrated nitric acid, in a sealed V4A stainless steel pressure vessel, are heated to 100° C in the course of 25 minutes, whilst stirring. The mixture is then stirred for 1 minute at this temperature and the pH value is then adjusted to 9.9 with 35 g of saturated sodium bicarbonate solution. 13 g of undissolved melamine are separated from the reaction product by filtration. The filtrate is worked up to a solids content of 76% (yield: 1,135 g) and has a flow cup viscosity of 230 seconds (4 mm flow cup at 20° C). The final product is miscible with water in all proportions.

EXAMPLE 27

The procedure is as in Example 26 but the mixture is stirred for a further 5 minutes after the temperature of 100° C has been reached. The solution obtained after neutralisation and cooling is completely clear. When worked up to a solids content of 75%, this gives 1,120 g of a product with a viscosity of 210 seconds (4 mm flow cup at 20° C) being miscible with water in all proportions.

EXAMPLE 28

The procedure is as in Example 27 but the amount of nitric acid is doubled. The crude reaction product is concentrated to 1,158 g (solids content 75%). The viscosity of this concentrate is 235 seconds (4 mm flow cup at 20° C) and it can be diluted with water in a ratio of 1:3.

EXAMPLE 29

316 g of melamine, 418 g of paraformaldehyde (90% strength), 2,000 g of methanol and 1 g of p-toluenesulphonic acid are heated to 100° C in a sealed container, and thus brought to an excess pressure of 2.4 atmospheres, in the course of 20 minutes, whilst stirring. The mixture is then stirred for 5 minutes under these conditions and thereafter the pH value is adjusted to 8.5 with 10 g of saturated sodium bicarbonate solution. The reaction product forms a clear solution (yield 740 g) which has a solids content of 85%, is miscible with water and isopropanol in all proportions, and has a viscosity of 183 poise at 25° C measured in an Epprecht viscometer.

EXAMPLE 30

474 g of melamine, 289 g of paraformaldehyde (90% strength), 1,933 g of methanol and 100 g of water are treated, after heating to 110° C and an excess pressure of 3.8 atmospheres, with 2.25 g of p-toluenesulphonic acid, dissolved in 20 g of methanol, and the mixture is then stirred for a further 8 minutes at this temperature. After neutralising with 20 g of sodium bicarbonate solution, cooling and working up to a solids content of 75%, a solution (yield 987 g) is formed which has a viscosity of 380 seconds (4 mm flow cup at 20° C) and is compatible with water in a ratio of 1:2.8.

EXAMPLE 31

316 g of melamine, 586 g of paraformaldehyde and 2,000 g of methanol are heated in a sealed container, whilst stirring, to 100° C, and to an excess pressure of 2.3 atmospheres in the course of 20 minutes, and a solution of 1 g of p-toluenesulphonic acid in 25 g of methanol is then added. The mixture thus produced is stirred for 6 minutes under these conditions, neutralised, cooled and worked up to a solids content of 86%. The resulting solution (yield 810 g) is miscible with water and isobutanol in all proportions and has a viscosity of 60 poise at 25° C, measured in an Epprecht viscometer.

EXAMPLE 32

378 g of melamine, 400 g of paraformaldehyde (90% strength) and 1,800 g of ethylene glycol monomethyl ether are heated in a sealed container to 95° C in the course of 45 minutes, whilst stirring, 2 g of concentrated nitric acid in 25 g of methanol are then added and the mixture is stirred for a further 10 minutes at 95° to 108° C. The reaction mixture is then rendered neutral with 40 g of a saturated sodium bicarbonate solution and worked up to a solids content of 72.4%. Yield: 1,355 g of a clear solution with a viscosity of 145 poise.

EXAMPLE 33

474 g of melamine, 124 g of paraformaldehyde (90% strength), 615 g of a mixture consisting of 36% of formaldehyde, 44% of water and 20% of methanol and 1,600 g of methanol are heated in a sealed container to 95° C, whilst stirring. A solution of 1.2 g of concentrated nitric acid in 26 g of methanol is then added and the mixture is further stirred at 95° C and under an excess pressure of 1.8 atmospheres. The pH is then adjusted to 8.6 with 30 g of a saturated sodium bicarbonate solution. On working up, 1,089 g of a 75% strength solution with a viscosity of 325 seconds, measured in a 4 mm flow cup at 20° C, are obtained.

EXAMPLE 34

378 g of melamine, 1,125 g of a solution of 40% of formaldehyde in isobutanol, 300 g of methanol and 1,000 g of isobutanol are heated to 100° C in a sealed autoclave a mixture of 2.0 g of concentrated nitric acid and 26 g of methanol is added and the reaction mixture is stirred for 10 minutes at 100° C. After neutralising with 40 g of saturated sodium bicarbonate solution, the mixture is cooled and concentrated to a solids content of 75%. (Yield: 1,312 g). The viscosity of the solution is 200 poise at 25° C, measured in an Epprecht rotating viscometer.

EXAMPLE 35

316 g of melamine, 502 g of paraformaldehyde (90% strength) and 2,000 g of methanol are heated to 100° C in 27 minutes in a closed container, 1 g of p-toluenesulphonic acid in 25 g of methanol is then added and the resulting mixture stirred for 9 minutes at 100° C. 10 g of saturated sodium bicarbonate solution are then added to the reaction mixture. Yield: 915 g (solids content = 75.3%) of a solution having a viscosity of 183 seconds, measured in a 4 mm flow cup at 20° C.

EXAMPLE 36

316 g of melamine, 1,156 g of (39% strength aqueous) formaldehyde solution and 1,500 g of methanol are heated to 100° C and an excess pressure of 1.75 atmospheres gauge in 23 minutes in a closed container, whilst stirring. 1 g of p-toluene-sulphonic acid, dissolved in 25 g of methanol, is then added and the resulting mixture is stirred for a further 9 minutes at 100° C, then neutralised with 10 g of saturated sodium bicarbonate solution and cooled. The final solution is evaporated and adjusted to a solids content of 75.7% (yield 925 g), has a viscosity of 210 seconds, measured in a 4 mm flow cup at 20° C.

EXAMPLE 37

474 g of melamine, 331 g of paraformaldehyde (90% strength), 413 g of a mixture consisting of 36% of formaldehyde, 44% of water and 20% of methanol and 1,600 g of methanol are heated in an autoclave to 110° C in 20 minutes, whilst stirring, the pressure rising to 3.25 atmospheres gauge. A solution of 1.2 g of concentrated nitric acid in 20 g of methanol is then pumped in and the mixture is stirred for a further 1 minute at 110° C. The pH value of the mixture is then rapidly adjusted to 8.6 with 30 g of a saturated solution of sodium bicarbonate in water and the final mixture is cooled. This gives 1,225 g of a 74.7% strength aqueous solution with a viscosity of 280 seconds, measured in a 4 mm flow cup at 20° C.

EXAMPLE 38

474 g of melamine, 331 g of paraformaldehyde (90% strength), 1,600 g of methanol and 413 g of a mixture consisting of 43% of water, 20% of methanol and 37% of formaldehyde are heated to 95° C in a sealed container, a pressure of 1.7 atmospheres gauge being set up. 3.53 g of formic acid in 20 g of methanol are then added and the mixture then stirred for 11 minutes at 95° C. The final solution is then rendered neutral with 55 g of a saturated solution of sodium bicarbonate in water, cooled and concentrated to a solids content of 75.4%. Yield: 1,250 g. Viscosity of the 75% strength solution: 400 seconds (4 mm DIN flow cup at 20° C).

EXAMPLE 39

The procedure is as in Example 38 but the acid is added at 105° C and thereafter the mixture is stirred for 5 minutes at this temperature. The product which has been neutralised and worked up to a solids content of 73.2% (902 g), has a flow cup viscosity of 235 seconds (4 mm DIN flow cup at 20° C).

EXAMPLE 40

298 g of melamine, 312 g of paraformaldehyde (90% strength), 2,000 g of methanol and 390 g of a mixture consisting of 20% of methanol, 37% of formaldehyde and 43% of water are heated in an autoclave to 95° C, whilst stirring, a solution of 1.2 g of concentrated nitric acid in 20 g of methanol is then added and the resulting mixture is stirred for 11 minutes at 95° C, neutralised with 30 ml of saturated sodium bicarbonate solution and cooled. After adjusting the product to a solids content of 75.6%, a clear solution (867 g) with a flow cup viscosity of 230 seconds (4 mm DIN flow cup at 20° C) is obtained.

EXAMPLE 41

474 g of melamine, 312 g of paraformaldehyde (90% strength), 1,600 g of methanol and 427 g of a mixture consisting of 20% of methanol, 37% of formaldehyde and 43% of water are heated to 90° C in an autoclave, whilst stirring, a pressure of 2.0 atmospheres gauge developing. A solution of 5 g of nitric acid ($d = 1.4$). in 25 g of methanol is then added and the resulting mixture is stirred for 5 minutes at 90° C, neutralised, and worked up, as indicated in the preceding Examples. This gives 1,230 g of a clear 75.4% strength solution with a viscosity of 132 seconds (4 mm DIN flow cup at 20° C).

EXAMPLE 42

374 g of benzoguanamine, 300 g of paraformaldehyde (90 % strength) and 2,000 g of methanol are heated to 95° C in a sealed container, 1.2 g of concentrated nitric acid are then added and the resulting mixture is stirred for 10 minutes at that temperature. It is then reached neutral with 35 g of concentrated sodium bicarbonate solution, cooled and concentrated to a solids content of 94%, and finally adjusted to a solids content of 74% by adding methanol. Yield: 744 g. of a solution having a viscosity of 80 seconds (4 mm DIN flow cup at 20° C).

EXAMPLE 43

474 g of melamine, 499 g of paraformaldehyde with a formaldehyde content of 90% and 2,200 g of n-propanol are heated, whilst stirring in a sealed pressure-resistant VA stainless steel vessel of 4,000 ml capacity, to 95° C in the course of 18 minutes. 1.2 g of concentrated nitric acid dissolved in 25 g of n-propanol are then introduced and the resulting mixture is stirred for a further 11 minutes at 95° C. After neutralising the resulting reaction mixture with 30 ml of saturated sodium bicarbonate solution, it is cooled and filtered, a residue of 42 g of unreacted melamine being separated off. After evaporation to 1,350 g, the filtrate had a solids content of 75% and a viscosity of 234 poise (25° C, Epprecht viscometer).

The solid resin in this product contained 4 mols of formaldehyde, 1.83 mols of which are etherified with n-propanol, per mol of melamine.

EXAMPLE 44

The reaction was carried out as in Example 43 but the mixture was stirred for 15 minutes instead of 11 minutes. In this case the residue of unreacted melamine is 16 g. Yield: 1,412 g of a 75% strength solution having a viscosity of 80 poise. Analytical data of the solid: 3.64 mols of formaldehyde and 1.94 mols of $OC_3H_7$ per mol of melamine.

EXAMPLE 45

474 g of melamine, 499 g of 90% strength paraformaldehyde and 2,200 g of n-propyl alcohol are heated to 100° C in the apparatus described in Example 43, in 30 minutes, a solution of 1.2 g of concentrated nitric acid in 25 g of n-propyl alcohol is then added and the resulting mixture is stirred for 15 minutes at 100° C. The mixture is then neutralised with sodium bicarbonate solution, cooled and concentrated to a solid content of 75%. This gives 1,500 g of a solution with a viscosity of 66 poise. No melamine residue remains when this procedure is used. The concentrated product can be diluted with xylene in a ratio of 1:9.4, with isobutanol in any proportion and with benzine in a ratio of 1:0.6. Analytical data: 3.69 mols of formaldehyde and 2.38 mols of $OC_3H_7$ per mol of melamine.

EXAMPLE 46

474 g of melamine, 998 g of 90% strength paraformaldehyde and 2,200 g of n-butanol are heated to 100° C in the apparatus of Example 43, in the course of 22 minutes and a solution of 1.2 g of concentrated nitric acid in 25 g of n-butanol is then added. Subsequently, the mixture is stirred for 15 minutes at 100° C and then neutralised with sodium bicarbonate solution. After concentrating the resulting product to a solids content of 75%, 2,100 g of a solution with a viscosity of 380 seconds (4 mm DIN flow cup at 20° C) are obtained.

EXAMPLE 47

344 g of benzoguanamine, 300 g of 90% strength paraformaldehyde and 2,200 g of methanol are heated in a sealed container to 95° C, a solution of 1.2 g of 63% strength nitric acid in 25 g of methanol is added and the resulting mixture is stirred for 10 minutes at 95° C. After neutralising the resulting mixture with 35 ml of saturated sodium bicarbonate solution, it is cooled and then concentrated to 558 g, and the residue is taken up in 282 g of isobutanol. A solution with a solids content of 62% and a viscosity of 167 seconds (4 mm DIN flow cup) is obtained.

EXAMPLE 48

Using a weight ratio of 100:15, the liquid resin mixture of Example 22 is sprayed onto both sides of a random fibre fleece made of polyester and weighing 60 g/m². The fleece is then dried for 10 seconds at 200° C and subjected to condensation. A fleece with outstanding strength and resilience is obtained.

EXAMPLE 49

The resin of Example 8 is added to an acrylate dispersion binder, containing hydroxyl groups and 25% solids, in a solids ratio of 100:20. 1% (based on total solids) of triethylammonium toluenesulphonate is then added and the resulting solution is padded (with a liquor pick-up of 100%) onto a polyester random fibre fleece. The fleece is then dried for 30 minutes at 80° C and subjected to post-condensation for 10 minutes at 130° C. The bonded fleece displays outstanding resistance to water and solvents as well as excellent tensile strength and resilience.

EXAMPLE 50

The resin solution obtained according to Example 21 is diluted with water to 58% solids content, and 1%, based on solids, of p-toluenesulphonic acid is added. A decorative paper weighing 80 g/m² is saturated to a resin content of 60 – 62% using this solution and dried to a residual moisture of 6%. The resin treated paper is pressed onto a chipboard for 10 minutes at 150° under a pressure of 20,000 ponds per square centimeter. A scratch-resistant, elastic and continuous surface is obtained.

EXAMPLE 51

This example illustrates the use of various etherified aminoplasts prepared according to the present invention, as crosslinking components for the manufacture of lacquer binders.

Various of the aminoplast and various types of other polymers containing hydroxyl groups were mixed in certain weight ratios. In all cases clear crosslinkable lacquer binders were obtained and were applied, in a layer thickness (wet) of 125μ, to a glass plate. In all cases colourless coatings with a high gloss and good properties were obtained after curing.

The table which follows gives a synopsis of the substances, ratios, preparation conditions, and properties of the cured coatings.

The columns of the table give the following data:

Column 1: No. of the example according to which the aminoplast was prepared.

Column 2: A letter which characterises the polymer containing hydroxyl groups.

Letter A: denotes a polyester, of the Alkydal F50W type, which is modified with fatty acid and isocyanate, can be diluted with water and has an acid number of 50.

Letter C: denotes an oil-modified alkyd resin with an acid number of <10 and which contains about 50% of synthetic fatty acids (Alftalat 421 C type), Letter L: denotes a short oil alkyd resin with 25% of synthetic fatty acids (Alkydal F25 type), Letter M: denotes an unmodified isophthalate polyester with an acid number of <5 and a OH number of ~150 of the Alftalat AN 100 type, Letter $S_1$: denotes a styrene/acrylate copolymer with 2% of hydroxyl groups, based on the solid resin. The acid number is less than 5 mg of KOH/g of solid resin.

Letter $S_2$: denotes a styrene/acrylate copolymer with 2% of hydroxyl groups, based on the solid resin. The acid number is about 20 mg of KOH/g of solid resin.

Letter $S_3$: denotes a styrene/acrylate copolymer with 2% of hydroxyl groups, based on the solid resin. The acid number is about 10 mg of KOH/g of solid resin.

Column 3: indicates the weight ratio solids basis of the polymer of Column 2 to the aminoplast of Column 1.

Column 4: indicates the curing conditions, the curing time (minutes) and the curing temperature (° C).

Column 5: gives a rating for the fingernail hardness of the cured coatings, the rating 0 denoting fingernail hard and the rating 1 denoting almost fingernail hard.

Column 6: indicates a rating on the known 6-stage cross-hatch assessment scale, 0 denoting the greatest adhesion to the substrate and 5 denoting the least adhesion to the substrate.

Column 7: indicates the state of the coating after subjecting it to the action of water for 24 hours, the rating 0 signifying no change in the coating, the rating 1 signifying a small decrease in the fingernail hardness and the rating 2 signifying a matt surface.

Column 8: indicates the state of the coating after subjecting it to the action of benzine for 24 hours, the ratings being as in column 7 and Column 9: indicates the solvent in which the aminoplast was dissolved.

TABLE

| Aminoplast | Polymer | Weight ratio Polymer to Aminoplast | minutes/ ° C | Fingernail hardness | Cross-hatch | Water resistance | Benzine-resistance | Solvent for the aminoplast |
|---|---|---|---|---|---|---|---|---|
| 45 | A | 65/35 | 30/120 | 0 | 5 | 0 | 0 | ⎫ |
| 45 | A | 70/30 | 30/120 | 0 | 0 | 0 | 0 | ⎬ n-propanol |
| 45 | M | 70/30 | 30/120 | 1 | 0 | 1 | 0 | ⎭ |
| 31 | A | 70/30 | 30/120 | 0 | 0 | 2 | 0 | isobutanol |
| 31 | A | 70/30 | 30/120 | 0 | 0 | 2 | 0 | water |
| 31 | M | 70/30 | 60/120 | 1 | 0 | 1 | 0 | isobutanol |
| 31 | C | 70/30 | 60/120 | 0 | 0 | 2 | 0 | water |
| 29 | A | 70/30 | 30/120 | 0 | 0 | 2 | 0 | water |
| 29 | L | 70/30 | 60/120 | 0 | 2 | 0 | 0 | water |
| 29 | C | 70/30 | 60/120 | 0 | 0 | 0 | 0 | water |
| 41 | A | 70/30 | 30/120 | 0 | 0 | 1 | 0 | water |

TABLE-continued

| Aminoplast | Polymer | Weight ratio Polymer to Aminoplast | minutes/ °C | Fingernail hardness | Cross-hatch | Water resistance | Benzine-resistance | Solvent for the aminoplast |
|---|---|---|---|---|---|---|---|---|
| 41 | L | 70/30 | 60/120 | 0 | 0 | 1 | 0 | water |
| 29 | M | 70/30 | 60/120 | 1 | 0 | 1 | 0 | } isobutanol |
| 41 | M | 70/30 | 60/120 | 0 | 0 | 1 | 0 | |
| 46 | A | 70/30 | 60/120 | 1 | 0 | 1 | 0 | n-butanol |
| 46 | M | 70/30 | 60/120 | 1 | 0 | 1 | 1 | n-butanol |
| 46 | L | 70/30 | 60/120 | 1 | 1 | 1 | 0 | n-butanol |
| 46 | C | 70/30 | 60/120 | 1 | 0 | 2 | 0 | n-butanol |
| 47 | A | 70/30 | 60/120 | 1 | 0 | 1 | 1 | isobutanol |
| 47 | M | 70/30 | 60/120 | 1 | 0 | 1 | 0 | isobutanol |
| 47 | L | 70/30 | 60/120 | 1 | 0 | 1 | 0 | isobutanol |
| 47 | C | 70/30 | 60/120 | 1 | 0 | 1 | 0 | isobutanol |
| 45 | L | 70/30 | 60/120 | 0 | 2 | 2 | 0 | } n-propanol |
| 45 | C | 70/30 | 60/120 | 0 | 0 | 2 | 0 | |
| 47 | $S_1$ | 70/30 | 60/120 | 1 | 4 | 0 | 0 | } isobutanol |
| 47 | $S_2$ | 70/30 | 60/120 | 1 | 2 | 0 | 0 | |
| 47 | $S_3$ | 70/30 | 60/120 | 1 | 4 | 1 | 1 | |
| 31 | $S_1$ | 70/30 | 60/120 | 1 | 0 | 0 | 0 | } isobutanol |
| 31 | $S_2$ | 70/30 | 60/120 | 0 | 5 | 0 | 0 | |
| 31 | $S_3$ | 70/30 | 60/120 | 1 | 0 | 1 | 1 | |
| 45 | $S_1$ | 70/30 | 60/120 | 1 | 0 | 0 | 0 | } n-propanol |
| 45 | $S_2$ | 70/30 | 60/120 | 0 | 5 | 0 | 0 | |
| 45 | $S_3$ | 70/30 | 60/120 | 1 | 0 | 1 | 1 | |
| 46 | $S_1$ | 70/30 | 60/120 | 1 | 0 | 1 | 1 | } n-butanol |
| 46 | $S_2$ | 70/30 | 60/120 | 1 | 5 | 0 | 0 | |
| 46 | $S_3$ | 70/30 | 60/120 | 1 | 1 | 1 | 1 | |

EXAMPLE 52

A vinyl acetate polymer, which contains hydroxyl groups and is in the form of a stable 50% aqueous emulsion, was treated with 15%, based on solids, of the product of Example 41 and with 1% of ammonium chloride. The water resistance of wood bonded with this mixture was improved to an outstanding degree.

What is claimed is:

1. In the process of preparing an etherified methylolaminotriazine resin concentrate from the aminotriazine, formaldehyde, an etherifying alcohol and an acid condensation catalyst, the improvement according to which those materials are interreacted in essentially a single step by mixing them in a proportion providing 0.77 to 3 mols of formaldehyde, 2.5 to 7 mols of alcohol having up to four carbons, and no more than 3 mols of water, for every mol of —$NH_2$ in the aminotriazine, at least 40 mol precent of the alcohol being methanol, heating the mixture in a closed container at a pressure at least as high as 0.1 atmosphere gauge and a temperature from about 85° to about 115° C, and terminating the condensation after 0.2 to 20 minutes of such heating.

2. The combination of claim 1, in which the condensation catalyst is a strong inorganic acid used in a proportion not higher than about 1 part per 1000 parts of reaction mixture.

3. The combination of claim 1 in which the etherifying alcohol is methanol and the reaction mixture contains a dissolved organic diluent that increases its boiling temperature but does not prevent condensation.

4. The combination of claim 1 in which the aminotriazine in melamine, the formaldehyde mixed is in the form of paraformaldehyde, and the heating is effected with the mixture under a pressure of at least 0.5 atmosphere gauge and at a pH between 4.5 and 6.5.

* * * * *